United States Patent [19]

Kupperman

[11] Patent Number: 4,760,737

[45] Date of Patent: Aug. 2, 1988

[54] PROCEDURE FOR FLAW DETECTION IN CAST STAINLESS STEEL

[75] Inventor: David S. Kupperman, Oak Park, Ill.

[73] Assignee: The United States of America as represented by the United States Department of Energy, Washington, D.C.

[21] Appl. No.: 902,912

[22] Filed: Aug. 29, 1986

[51] Int. Cl.<sup>4</sup> .............................................. G01N 29/00
[52] U.S. Cl. .......................................... 73/622; 73/799
[58] Field of Search ................. 73/622, 570, 596, 799, 73/597, 598, 599, 600

[56] References Cited

U.S. PATENT DOCUMENTS

| | | | |
|---|---|---|---|
| 3,921,440 | 11/1975 | Toth | 73/622 |
| 4,331,034 | 5/1982 | Takeda et al. | 73/637 |
| 4,539,848 | 9/1985 | Takafaji | 73/599 |

OTHER PUBLICATIONS

Kupperman, D. S. et al., The Application of Ultrasonic Steel, Taylor Publishing Co. Dallas, Texas, 1985.

*Primary Examiner*—Jerry W. Myracle
*Attorney, Agent, or Firm*—Michael Higgins; John M. Albrecht; Judson R. Hightower

[57] ABSTRACT

A method of ultrasonic flaw detection in cast stainless steel components incorporating the steps of determining the nature of the microstructure of the cast stainless steel at the site of the flaw detection measurements by ultrasonic elements independent of the component thickness at the site; choosing from a plurality of flaw detection techniques, one such technique appropriate to the nature of the microstructure as determined and detecting flaws by use of the chosen technique.

16 Claims, 3 Drawing Sheets

PROCEDURE FOR FLAW DETECTION IN CAST STAINLESS STEEL

CONTRACTUAL ORIGIN OF THE INVENTION

The United States Government has rights in this invention pursuant to Contract No. W-31-109-ENG-38 between the U.S. Department of Energy and the University of Chicago.

BACKGROUND OF THE INVENTION

State and federal regulations require rigorous inspection of nuclear power plants. Inspections must be carried out both before the plant is put in initial service and subsequently during periodic plant shutdowns. Among the more critical components of a nuclear power plant are the complex stainless steel piping systems which may comprise individual sections of cast stainless steel (CSS) pipe welded together. Such piping systems typically carry reactor coolants which may be radioactive. The integrity of such piping is thus a critical aspect of the safe operation of a nuclear power plant.

Because non-destructive examination (NDE) involving radiographic methods is not practical in the generally radio-active atmosphere within a nuclear power plant, regulations commonly require that ultrasonic testing be employed for initial and subsequent testing of CSS piping components. Ultrasonic testing generally involves launching an elastic wave pulse into the volume of the component being tested and detecting reflected pulses. Typically, soundwaves will be reflected from various geometric reflectors, some of interest, such as flaws to be detected, and some which constitute noise, such as normal geometric boundaries in the structure and acoustical discontinuities in the granular microstructure of the material. In addition, the microstructure of the material, depending upon its nature, may cause distortion or attenuation of the reflected signals further complicating the testing.

The typical flaws or degradation in cast stainless steel piping are the result of intergranular stress-corrosion cracking or fatigue cracks most often occuring in the vicinity of weldments. These flaws may be very tight cracks through the material. The ultrasonic signals reflected from such flaws are often small in amplitude and difficult to distinguish from other reflected signals, particularly the noise resulting from the normal microstructure of the material.

If the character of the microstructure of the material to be tested is known or if calibration specimens having the same structure as the material to be tested are available, the ultrasonic testing apparatus and technique may be adapted by one skilled in the art to optimize flaw detecting efficiency. The problem of applying such techniques to the in situ inspection of CSS piping in nuclear power plants is that the microstructure of the CSS in not uniform. The microstructure of CSS varies from elastically isotropic with equiaxed, relatively small grains to elastically anisotropic with columnar grains oriented radially with respect to the cross-section of the pipe. Variations may occur from one pipe component to another or longitudinally or circumferencially along a single pipe component. In addition, the microstructure may be some combination of the two extremes described.

In order to optimize the ultrasonic flaw detection in CSS piping, it is necessary to first determine the nature of the microstructure at each individual test site. This has not heretofore been possible in an automated ultrasonic scanning device. For example, the microstructure of the pipe may be determined by measuring the skew in the path of a soundwave reflected from the inner wall of the pipe. Since it is known that the velocity of elastic waves depend upon the direction of propagation relative to the axis of the microstructure grains within a material, an anisotropic material will exhibit greater skewing of elastic waves than an isotropic material. This technique, however, requires accurate knowledge of the wall thickness of the pipe. For cast stainless steel pipe used in nuclear power plants, this technique is not useful because the tolerances in the pipe wall thickness are too large.

Because of these difficulties, a conservative approach toward replacement of potentially flawed pipes in nuclear power plants has thus been necessary. Replacement of piping in nuclear power plants is an expensive proposition, particularly when it involves unplanned or extended shut-down of the reactor and consequential loss of revenue for the utility.

Accordingly, it is an object of the present invention to provide a more reliable NDE method for inspection of components of nuclear power plants. It is a further object of this invention to provide an improved method for ultrasonic testing of cast stainless steel piping components in a nuclear power plant. It is still another object of this invention to provide an apparatus for improved in situ ultrasonic testing of cast stainless steel pipe in nuclear power plants. It is another object to provide a method for determining the microstructure of cast stainless steel piping components independent of the dimensions of such components whereby such determination facilitates the choice of a more reliable technique for flaw detection.

SUMMARY OF THE INVENTION

The present invention involves a method of detecting flaws in cast stainless steel piping in which one of a plurality of conventional flaw detection techniques is chosen and employed depending upon prior determination of the character of the microstructure of the cast stainless steel at the site of the detection measurement. A principal novel aspect of the invention features an ultrasonic measurement technique for a characterization of the microstructure that is independent of the thickness of the sample.

In accordance with the invention an ultrasonic signal is transmitted by means of a transducer into the volume of the material to be tested, the ultrasonic signal having primary and secondary waves propagating in different directions through the material. By means of a second receiving transducer the relative position of the reflected primary and secondary waves are determined, from which data the character of the microstructure of the material is determined. Depending upon the character of the microstructure as determined, one of a plurality of flaw detection methods is chosen and the material is inspected with such method. Also provided is an apparatus for carrying out the inspection method provided by the invention.

DETAILED DESCRIPTION OF THE PREFERRED EMBODIMENTS

Figure 1:
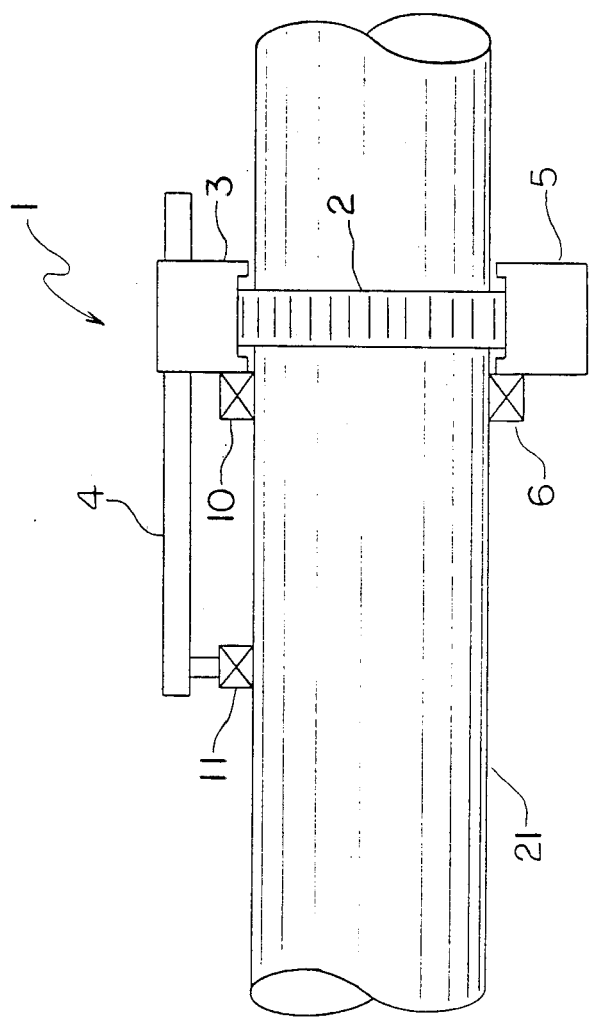
FIG. 1 is a side view of a preferred embodiment of an ultrasonic testing apparatus adapted to carrying out the testing method of this invention. The apparatus is shown mounted on a pipe.

The ultrasonic scanning apparatus depicted in FIG. 1 illustrates an embodiment comprising a novel combination of conventional ultrasonic testing components adapted to carrying out the basic method involved in this invention. In order to better understand the essential novelty of the combination, the novel ultrasonic testing method will first be described in detail.

It will be useful to first describe the basic manual ultrasonic testing procedure. Conventional ultrasonic probing involves a sending transducer for launching an elastic wave pulse into the material to be tested and a receiving transducer for receiving reflections of the pulse as well as an oscillator for exciting the wave in the sending transducer and an oscillscope display means to show the amplitude of the incident pulse and received reflections on a time scale which may be callibrated to be analogous to the depth of the reflecting feature within the material. Variations in the basic technique include using the same transducer for sending and receiving, the so-called pulse echo mode; or using separate sending and receiving transducers, the so-called pitch-catch mode; the frequency of the elastic wave may be varied; the size of the transducers may be varied; the angle at which the pulse is propagated relative to a normal to the surface of the material tested may be varied; the wave pulse may comprise longitudinal (compression) waves or shear waves. Choice among all these variables is a matter for one skilled in the art and depends upon the material being probed, the nature of the physical features to be detected, and the dimensions of the component undergoing examination and other environmental factors.

In "The application of Ultrasonic Waves to Assess Grain Structure in Cast Stainless Steel" Kupperman, et al., Proceedings of the World Conference on Nondestructive Testing, Volume 3, Nov. 8, 1985, p. 1685, incorporated herein by reference, it is reported that in CSS with isotropic microstructure, flaw detection using vertical shear waves is most effective and in CSS with anisotropic microstructure and columnar grains, flaw detection using longitudinal waves is most effective.

For isotropic microstructure, the preferred method of flaw detection is with a 45° vertical shear wave probe operated in a pulse echo mode at about 0.5 MHZ. For anistropic materials the preferred method is with a 45° longitudinal wave probe in a pitch-catch mode at about 1 MHZ.

The signal to noise ratio in detecting a typical flaw in a sample specimen was reported to be of comparable magnitude in both cases using the preferred method of detection. When longitudinal waves were used with isotropic material or shear waves with anisotropic material, the signal to noise ratio was typically one half of that for the preferred method.

Figure 2:
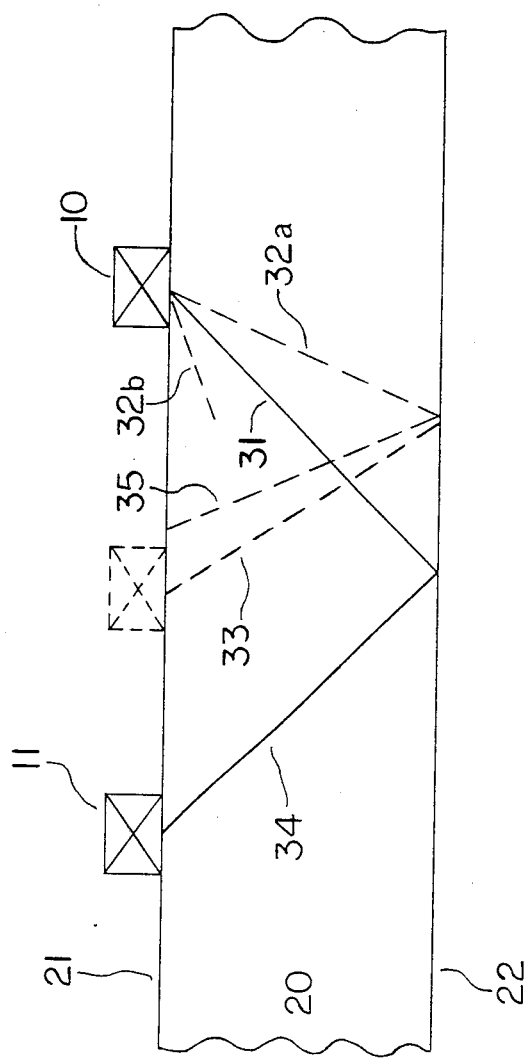
FIG. 2 is a side view of the pipe wall showing an ultrasonic sending transducer and an ultrasonic receiving transducer and the paths of primary and secondary elastic waves through the pipe wall.

The novel method of ultrasonic testing of cast stainless steel of this invention comprises the steps of determining the microstructure of the material at the site to be tested, then choosing a flaw detection technique appropriate to the nature of the material. The first step, determining the microstructure, will be described with reference to FIG. 2. In FIG. 2, sending transducer 10 and receiving transducer 11 are depicted coupled to the pipe wall 20, in a manner well known in the art, at the outer surface 21 of said pipe wall. Also depicted are the paths of propagation of various incident and reflected wave pulses. Sending transducer 10 is a 45° angle beam transducer that produces elastic vertical shear wave (SV wave) pulse at a frequency of approximately 0.5 MHz. The sending transducer is a relatively large probe, approximately one inch by one inch, so that the beam produced undergoes considerable spreading. Thus, in addition to the primary 45° SV wave 31, there are also less intense SV waves 32a and 32b at steeper and shallower angles respectively. Part of the wave propagated at an angle of incidence of about 21° undergoes mode conversion upon reflection at the inner wall 22 of the pipe in accordance with Snell's law. This produces a reflected wave comprising L and SV components. In an isotropic equiaxed grain CSS, the receiving transducer 11 will detect a primary reflected SV wave 34 at a position approximately twice the thickness of the sample from the sending transducer and will detect the secondary reflected L wave 33 at a distance approximately one times the thickness of the material from the sending transducer. In a columnar grain, anisotropic CSS, the position of the reflected primary wave 35, being a pure SV wave, will be skewed closer to the sending transducer, since the velocity of a SV wave is higher for propagation parallel to the columnar grain axis. The secondary reflected wave comprising both SV and L components is separated into separate components with the SV component 35 being skewed toward the sending transducer and the longitudinal component 33 skewed slightly away from the sending transducer. In some cases the primary wave will be detected in a position closer to the sending transducer than the secondary longitudinal wave. The relevant primary and secondary reflected wave pulses may be identified by means of the relative transit times in the usual manner since the relative transit time for a given wave type is independent of skewing.

Figure 3A:
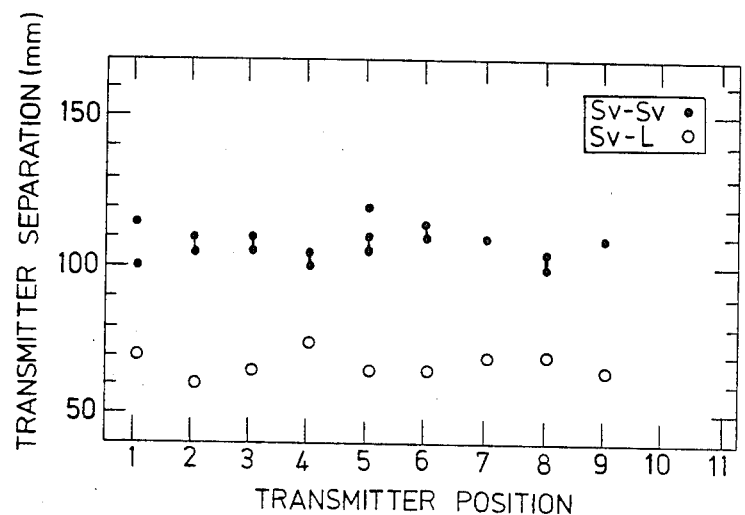
FIG. 3a is a graph showing the separation between the primary and secondary reflected waves for a cast stainless steel sample with predominantly equiaxed grains and isotropic microstructure.
Figure 3B:
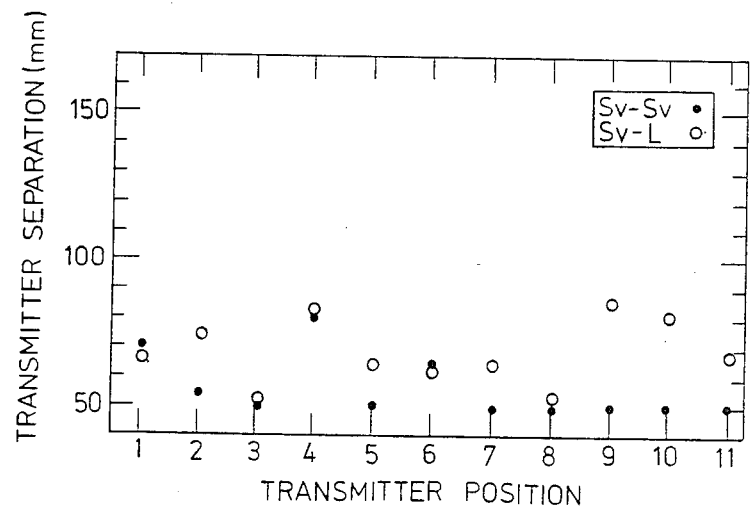
FIG. 3b is a graph showing the separation between primary and secondary reflected waves for a cast stainless steel sample with predominantly columnar grains and an isotropic microstructure.

FIG. 3a and 3b represent graphically the separation between the sending transducer and the receiving transducer when the receiving transducer is in position to receive the primary reflected SV wave (solid circle) and the secondary reflected L wave (open circle). The vertical axis represents distance from the sending transducer. The horizontal axis represents successive test positions across the test specimen. The data depicted in FIG. 3a is from a CSS specimen with predominantly isotropic microstructure with equiaxed grains with a thickness of approximately 60 mm. The separation between the sending transducer and the position where the primary reflected SV wave was detected is approximately twice the thickness of the sample and the relative position of the secondary reflected L wave is clearly about half way between the sending transducer and the primary reflected SV wave. In FIG. 3b, the CSS specimen had a predominantly anisotropic microstructure with columnar grains parallel to the thickness of the specimen. Here it is noted that the primary reflected SV wave is skewed toward the sending transducer, in most cases actually closer to the sending transducer than the secondary reflected L wave.

The method of the present invention may be accomplished by launching an SV wave at approximately 45° to the normal surface of the material to be tested by means of sending transducer 10 as described above. The primary SV wave reflected from the opposite wall of the material is detected with receiving transducer 11 and the position of the received signal relative to that of the sending transducer is determined. Next, the secondary L wave reflected from the opposite side is detected with receiving transducer 11 and the relative position is determined. By means of these data, it is determined whether the material is an isotropic or anisotropic microstructure. If the material has an isotropic microstructure ultrasonic flaw detection is carried out using an SV wave probe as described above. If the microstructure of the material is determined to be anisotropic, ultrasonic flaw detection is carried out using an L wave probe as described above. If the microstructure of the material is determined to be anisotropic, ultrasonic flaw detection is carried out using an L wave probe as described above.

With reference to FIG. 1, an ultrasonic scanning apparatus 1, adapted to perform the novel method of the present invention comprises an annular guide rail 2 mounted in an enclosing relationship around a tubular component 21 to be probed. A first carriage 3 is mounted to the guide rail 2 and is circumferentially movable thereon. The carriage 3 includes circumferential driving means. A second carriage 5 is also mounted to guide rail 2 and includes circumferential driving means. Sending transducer 10 is mounted in a fixed relationship to carriage 3 such that the transducer 10 is acoustically coupled to the surface of the tubular component 21 and will move circumferentially about the tubular component 21, remaining acoustically coupled thereto, as carriage 3 moves circumferentially. Rail member 4 is movably attached to carriage 3 which also contains means for longitudinally moving the rail member 4 with respect to the tubular component 21. Receiving transducer 11 is mounted to rail member 4 in a fixed relation and is disposed to be acoustically coupled to the tubular component 21 such that the receiving transducer 11 is moved longitudinally along the surface of the tubular component when the rail member is moved longitudinally. The receiving transducer 11 will also move circumferentially about the tubular component 21 as carriage 3 moves circumferentially. A plurality of ultrasonic flaw detection means 6 are mounted in a fixed relationship to second carriage 5 such that each of said ultrasonic flaw detection means is acoustically coupled to the surface of the tubular component and circumferentially movable with respect thereto along with second carriage 5.

Mechanisms for the various components of this apparatus are conventional and well known in the art. For example, U.S. Pat. No. 4,331,034 by Takeda et al. discloses an ultrasonic probing apparatus and includes a detailed mechanical description of similar components. These mechanical details are not related to the novel aspects of the invention claimed in the present application.

The operation of the apparatus of FIG. 1, will now be described. An elastic SV wave pulse is launched into the wall of the tubular component 21 by means of the sending transducer 10, the characteristics of which are described in the above description of the method of the present invention. Receiving transducer 11 is positioned to receive the reflected primary SV wave by moving the rail member 4 longitudinally with the longitudinal moving means in first carriage 3. The position where said reflected primary SV wave is received, is sensed by conventional position sensing means (not shown) in carriage 4 and such data is collected by suitable conventional data collecting means (not shown). Rail member 4 is then moved by the longitudinal motion means to position receiving transducer 11 in a second position to receive the reflected secondary L wave and such position is sensed and the data collected. The position data for the reflected primary SV wave and the reflected secondary L wave are then processed by suitable data processing means to determine the nature of the microstructure of the material at the measurement site on the tubular component 21 and based on the nature of the microstructure, choose the preferred one of the plurality of ultrasonic flaw detection probe means 6 to test for flaws. In an alternative embodiment, the plurality of ultrasonic flaw detection means 6 may be mounted on first carriage 3. Circumferential position sensing means may be provided for positioning the chosen ultrasonic flaw detection probe means at the site where the microstructure was determined. The circumferential moving means provided for each of first carriage 3 and second carriage 5 enables the apparatus to be repositioned to scan a plurality of sites about the circumference of tubular component 21, using the preferred flaw detection method depending upon the nature of the microstructure of the metal at each site.

It will be recognized by those skilled in the art, that the foregoing description is illustrative of the principles of the present invention. Since numerous modifications will be readily apparent to those skilled in the art, it is not intended to limit the invention to the exact construction described.

The embodiments of this invention in which an exclusive property or privilidge is claimed are defined as follows;

1. A method of detecting flaws in the wall of a tubular metal component in which the microstructure of the metal of the component may vary at different locations on the metal component from elastically isotropic with equiaxed grains to elastically anisotropic with columnar grains and further in which there is a plurality of ultrasonic flaw detection means each of which alternately provide the most effective result as applied to the different microstructures of the metal comprising:

determining at one location on the component the nature of the microstructure of the metal by an ultrasonic method;

inspecting said tubular metal component at the one location for flaws with the one ultrasonic flaw detection means of the plurality of ultrasonic flow detection means which provides the most effective result based upon the microstructure so determined whereby the component can be inspected for flaws at a particular location.

2. The method of claim 1 wherein the ultrasonic method for determining the nature of the microstructure of the metal is further characterized as comprising the steps of:

transmitting an ultrasonic wave signal having primary and secondary waves from a first transducer means into the wall of the tubular metal component at one surface of said wall;

receiving reflections of said primary and secondary ultrasonic waves from the opposite surface of said wall with a second transducer means;

collecting data associated with the relative positions of said first and second transducer when said reflected ultrasonic wave signals are received whereby the nature of the microstructure of the metal can be determined.

3. The method of claim 2 wherein said first transducer means comprises a 45° shear wave transducer means for producing an elastic shear wave at a frequency in the range of 0.5 to 1.0 MHz.

4. The method of claim 3 wherein said plurality of ultrasonic flaw detection means includes a first detection means comprising a 45° shear wave probe operated in a pulse-echo mode at a frequency of 0.5 MHz and a second detection means comprising a 45° longitudinal wave probe operated in a pitch-catch mode at a frequency of 1.0 MHz.

5. The method of claim 1 further characterized as comprising the step of:

examining the tubular metal component for flaws at another location by the method used at the first location.

6. An apparatus for ultrasonic scanning of a tubular metal component in which the microstructure of the metal may vary from elastically isotropic with equiaxed grains to elastically anisotropic with columnar grains, comprising:

a first ultrasonic transducer for launching an ultrasonic signal having primary and secondary vertical shear waves into the volume of said metal component;

a second ultrasonic transducer for receiving reflections of said ultrasonic signal;

means for relatively moving said first and second ultrasonic transducers on the surface of said tubular metal component;

means for collecting data associated with the relative positions of said first and second ultrasonic transducers;

means for applying said data to determine the microstructure of the tubular metal component in accordance with preselected criteria;

plurality of different ultrasonic flaw detecting probe means; and means for positioning said first and second ultrasonic transducers and said plurality of ultrasonic flaw detecting probe means about said tubular metal component to scan a plurality of sites thereon.

7. The apparatus of claim 6 further characterized as including:

an annular guide rail adapted for mounting in an enclosing relationship around said tubular component;

a first carriage mounted to said guide rail and circumferentially movable thereon, on which said first ultrasonic transducers means is mounted in a fixed relationship thereto and disposed such that said transducer is acoustically coupled to said tubular component;

driving means for circumferentially moving said carriage about said guide rail;

a rail member movably mounted on said carriage, on which said second ultrasonic transducer means is mounted disposed such that said transducer is acoustically coupled to said tubular component;

moving means for longitudinally moving said rail member with respect to said carriage such that said second transducer is movable longitudinally along said said tubular component relative to said first transducer;

a second carriage means mounted to said guide rail and circumferentially movable thereon on which each of said plurality of different ultrasonic flaw detecting probe means is fixedly mounted and disposed such that each of said probe means is acoustically coupled to said tubular component.

8. The apparatus of claim 7 wherein said plurality of different ultrasonic flaw detecting probe means includes a first ultrasonic flaw detecting probe comprising a 45° vertical shear wave probe operated in a pulse-echo mode and a second ultrasonic flaw detecting probe means, comprising a 45° longitudinal wave probe operated in a pitch-catch mode.

9. A method for determining the microstructure of a tubular metal component in which the microstructure of the metal may vary from elastically isotropic with equiaxed grains to elastically anisotropic with columnar gains comprising the steps of:

transmitting an ultrasonic wave signal having primary and secondary waves from a first transducer means into the wall of the tubular metal component at one surface of said wall;

receiving reflections of said primary and secondary ultrasonic waves from the opposite surface of said wall with a second transducer means;

collecting data associated with the relative positions of said first and second transducer when said reflected ultrasonic wave signals are received whereby the nature of the microstructure of the metal can be determined.

10. The method of claim 9 wherein said first transducer means comprises a 45° shear wave transducer means for producing an elastic shear wave at a frequency in the range of 0.5 to 1.0 MHz.

11. An apparatus for ultrasonic scanning of a tubular metal component in which the microstructure of the metal of the component may vary from elastically isotropic with equiaxed grains to elastically anisotropic with columnar grains comprising:

means for determining the microstructure of the tubular metal component at a particular location;

a plurality of flaw detection means each of which provides a different level of sensitivity depending upon the type of microstructure;

correlation means associating the type of microstructure determined at the particular location with the one of said plurality of flaw detection means which provides the highest level of sensitivity whereby the tubular metal component can be examined for flaws with a high degree of sensitivity at the particular location.

12. The apparatus of claim 11 in which said means for determining the microstructure comprises:

a first ultrasonic transducer positioned on the tubular metal component and a second ultrasonic transducer positioned on the tubular metal component whereby the nature of the microstructure can be determined by the relative positions of said first and said second ultrasonic transducers on the tubular metal component if an ultrasonic wave were launched from said first ultrasonic transducer and received by said second ultrasonic transducer.

13. The apparatus of claim 12 in which said plurality of flaw detection means comprises:
    ultrasonic flaw detection by means of vertical shear waves;
    ultrasonic flaw detection by means of longitudinal waves.

14. The apparatus of claim 13 in which said correlation means comprises:
    means for associating use of ultrasonic flaw detection by means of vertical shear waves with cast stainless steel determined to be isotropic;
    means for associating use of ultrasonic flaw detection by means of longitudinal waves with cast stainless steel determined to be anisotropic.

15. The apparatus of claim 14 including:
    an annular guide rail which can be rigidly affixed around and enclose the tubular metal component to be examined;
    a carriage mounted upon said annular guide rail and capable of moving circumferentially thereon and to which said first ultrasonic transducer is mounted.

16. The apparatus of claim 15 including:
    a rail member attached to one end to said carriage and at the other end to said second ultrasonic transducer and capable of moving said second transducer longitudinally along the tubular metal component with respect to said carriage.

* * * * *